US010376490B2

(12) United States Patent
Wu et al.

(10) Patent No.: US 10,376,490 B2
(45) Date of Patent: Aug. 13, 2019

(54) PHARMACEUTICAL COMPOSITION CONTAINING SILYBIN

(71) Applicant: TASLY PHARMACEUTICAL GROUP CO., LTD., Tianjin (CN)

(72) Inventors: Naifeng Wu, Tianjin (CN); Xijun Yan, Tianjin (CN); He Sun, Tianjin (CN); Kaijing Yan, Tianjin (CN); Yonghong Zhu, Tianjin (CN); Shunnan Zhang, Tianjin (CN); Xiaolin Bai, Tianjin (CN); Yi He, Tianjin (CN); Xiaohui Ma, Tianjin (CN); Ting Li, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 15/560,578

(22) PCT Filed: Mar. 22, 2016

(86) PCT No.: PCT/CN2016/077039
§ 371 (c)(1),
(2) Date: Sep. 22, 2017

(87) PCT Pub. No.: WO2016/150380
PCT Pub. Date: Sep. 29, 2016

(65) Prior Publication Data
US 2018/0042893 A1 Feb. 15, 2018

(30) Foreign Application Priority Data
Mar. 23, 2015 (CN) .......................... 2015 1 0127265

(51) Int. Cl.
*A61K 9/00* (2006.01)
*A61K 9/14* (2006.01)
*A61K 9/16* (2006.01)
*A61K 9/20* (2006.01)
*A61K 9/48* (2006.01)
*A61K 36/82* (2006.01)
*A61K 47/24* (2006.01)
*B65D 81/32* (2006.01)
*A61K 31/357* (2006.01)

(52) U.S. Cl.
CPC .......... *A61K 31/357* (2013.01); *A61K 9/0095* (2013.01); *A61K 9/145* (2013.01); *A61K 9/1617* (2013.01); *A61K 9/2013* (2013.01); *A61K 9/4858* (2013.01); *A61K 36/82* (2013.01); *A61K 47/24* (2013.01); *B65D 81/32* (2013.01); *A61K 2236/19* (2013.01)

(58) Field of Classification Search
CPC ................ A61K 36/82; A61K 2236/19; A61K 2236/30; A61K 9/1617; A61P 1/16; A23F 3/34; A23L 19/03; A23L 33/105
See application file for complete search history.

(56) References Cited

U.S. PATENT DOCUMENTS

| 4,764,508 A * | 8/1988 | Gabetta .............. C07D 407/04 514/78 |
| 2004/0023894 A1* | 2/2004 | Hasler-Nguyen ......... A23L 2/52 514/27 |
| 2018/0000965 A1 | 1/2018 | Chen et al. |
| 2018/0042892 A1 | 2/2018 | Wu et al. |
| 2018/0050015 A1 | 2/2018 | Sun et al. |
| 2018/0055817 A1 | 3/2018 | Sun et al. |
| 2018/0104215 A1 | 4/2018 | Sun et al. |
| 2018/0104216 A1 | 4/2018 | Yan et al. |
| 2018/0127445 A1 | 5/2018 | Wang et al. |
| 2018/0153848 A1 | 6/2018 | Chen et al. |
| 2018/0162860 A1 | 6/2018 | Gao et al. |
| 2018/0179222 A1 | 6/2018 | Wang et al. |
| 2018/0256450 A1 | 9/2018 | Yan et al. |
| 2018/0263851 A1 | 9/2018 | Yan et al. |
| 2018/0371004 A1 | 12/2018 | Wang et al. |

FOREIGN PATENT DOCUMENTS

| BY | 17987 C1 | 2/2014 |
| CN | 1961874 A | 5/2007 |
| CN | 100594898 C | 3/2010 |
| CN | 101961059 A | 2/2011 |
| CN | 101961060 A | 2/2011 |
| CN | 101961061 A | 2/2011 |
| CN | 101961425 A | 2/2011 |
| CN | 103372169 A | 10/2013 |
| CN | 103655929 A | 3/2014 |
| CN | 103751785 A | 4/2014 |
| CN | 103751798 A | 4/2014 |
| CN | 103830204 A | 6/2014 |

(Continued)

OTHER PUBLICATIONS

Yang et al.; "Study of the treatment of non-alcoholic fatty liver disease"; Journal of Traditional Chinese Medicine; vol. 31 No. 7; Jul. 2011; p. 621-622 (English Translation).
Chen et al.; "Research progress of natural polyphenol elements"; World Phytomedicines; vol. 12 No. 1; 1997; p. 9-15 (English Translation).
International Patent Application No. PCT/CN2016/077039; Int'l Written Opinion and Search Report; dated Jun. 21, 2016; 7 pages.
U.S. Appl. No. 16/073,507, dated Jul. 27, 2018, Han et al.
Malaguarnera et al.; "Myocardial oxidative stress in an experimental model of nonalcoholic fatty liver disease: role of silibinin"; FEBS Journal; vol. 278; 2011; p. 465.

(Continued)

*Primary Examiner* — Mark V Stevens
(74) *Attorney, Agent, or Firm* — Baker Hostetler

(57) ABSTRACT

A pharmaceutical composition for treating non-alcoholic fatty liver diseases consists of a silybin-phospholipid complex preparation and Pu'er tea/tea product according to a weight ratio of 0.5-2.5:0.3-10, wherein the silybin-phospholipid complex capsule preparation and the Pu'er teat/tea product are separately packaged.

17 Claims, No Drawings

(56) References Cited

FOREIGN PATENT DOCUMENTS

| | | |
|---|---|---|
| EP | 0209037 A1 | 1/1987 |
| RU | 2314797 C2 | 1/2008 |
| RU | 2318538 C1 | 3/2008 |
| WO | WO 2014/147119 A1 | 9/2014 |

OTHER PUBLICATIONS

Hu et al.; "Preventive Effect of Silibinin in combination with Pu-erh tea extract on nonalcoholic fatty liver disease in ob/ob mice"; Food and Nutrition; vol. 8; 2017; p. 1105-1115.

Koo et al.; "Effects of Camellia sinensis Extracts on the Antioxidant System and Alcohol Down-Regulation Enzymes in Sub-Acute Ethanol Treated ICR Mice"; Journal of the Korean Society of Food Science and Nutrition; vol. 36 No. 9; 2007; p. 1134-1139 (English Abstract).

Grattagliano et al.; "A silybin-phospholipids complex counteracts rat fatty liver degeneration and mitochondrial oxidative changes"; World Journal of Gastroenterology; vol. 19 No. 20; May 2013; p. 3007-3017.

Abascal et al.; "Kudzu—the Miracle Vine"; Alternative & Complementary Therapies; Apr. 2007; p. 78-85.

\* cited by examiner

PHARMACEUTICAL COMPOSITION CONTAINING SILYBIN

CROSS-REFERENCE TO RELATED APPLICATIONS

This application is the National Stage of International Application No. PCT/CN2016/077039 filed Mar. 22, 2016, which claims the benefit of Chinese application number 201510127265.2, filed Mar. 23, 2015 the disclosures of which are incorporated herein by reference in their entireties.

TECHNICAL FIELD

The present invention relates to the technical field of medicines, and particularly to a pharmaceutical composition containing silybin for the treatment of hepatopathy.

BACKGROUND ART

In the late 1960s and 1980s, the pharmaceutists of West Germany with H. wagner as representative extracted the active ingredient from the fruit of the Silybummarianum, which is named as silymarin, a new class of flavonoid having a C-9 substituents, i.e., a flavonoid lignans condensed with a dihydroflavonol and a phenylpropanoid derivative. Silybin(silibinin) is one of the main components of silymarin. Pharmacological and toxicological studies have shown that silybin has the effects of protecting and stabilizing the hepatocyte membrane, promoting the recovery of hepatocyte and improving the liver function. Silybin has different levels of protection and treatment effects on various types of hepatic injury caused by hepatic poisons such as carbon tetrachloride, thioacetamide, hydroxycholine, phalloidine, mucronatine, etc. And silybin can be used for treating acute and chronic hepatitis, early hepatocirrhosis, fatty liver, toxic or drug-induced hepatopathy.

The silybin is poor in water solubility and common organic solvents, resulting in low bioavailability and thereby affecting the clinical efficacy. To improve the bioavilability thereof, domestic and external pharmacy workers have made substantial amounts of work. The measures to improve the absorption of poorly soluble drugs are typically superfine grinding, salinization, and the addition of cosolvent, etc. In recent years, the studies have shown that the dissolution and bioavailability are greatly improved by the methods of formulating into cyclodextrin inclusion compound, solid dispersion, synthetic phospholipid complex and formulating into different dosage forms.

From the perspective of solid preparation, the phospholipid complex is a more specific solid dispersion, which has a fixed melting point, is a molecular compound (complex) whose chemical nature is more stable and different from the compound of drug and phospholipid, such compounds varies with the types of phospholipid and ratios of drug to phospholipid, and a phospholipid molecule can be bound with a different number of drug molecules. Deduced from the spectroscopy characteristics of the complex, the drug has a strong interaction with the polar groups of the phospholipid, which inhibits the free rotation of the single chains in the molecule, whereas the two long fatty acid chains of the phospholipid do not participate in the complex reaction and are free to shift and wrap the polar portions of the phospholipid to form a lipophilic surface, so that the complex shows strong lipid solubility. The complex changes the physiochemical properties of drug, and thus increases the lipid solubility of the drugs and reduces the water solubility of the drugs, and promotes the combination of drug molecules and cell membranes to improve the absorption and increases the bioavailability of the drug.

Pu'er tea is a unique and famous tea in Yunnan province. The locality has moderate climate, abundant rainfall and is mist-shrouded. Pu'er tea is divided into two series by Yunan big leaf species sun-dry tea and reprocessing thereof: the unzymic Pu'er tea by directly re-processing into the finished product and the enzymic Pu'er tea by re-processing after the artificial accelerated fermentation, and the patterns of which are divided into loose tea and compressed tea; natural aging process is also persistently carried out after the finished products, with the unique qualities gets better.

Pu'er tea is the only post-fermented tea, and substances harmful to the human body such as theophylline, tea polyphenols are degraded in the long process of fermentation, so the product is mild, does not stimulate the body, and also can promote metabolism, accelerate the digestion and transformation of fats and toxins in the body. For the problems of obesity and three-hypes which are puzzling urbanites, Pu'er tea can play a good mitigation effect, such as expelling of toxin, nourishing the stomach, anti-inflammatory, reducing the cholesterol, off lipid and removing grease, cosmetic slimming. Modern technologies show that Pu'er tea can improve insulin resistance, regulate levels of blood lipid and leptin, etc., and can block the fat accumulation of hepatic parenchymal cell caused by insulin resistance to some extent.

Non-alcoholic fatty liver disease (NAFLD) is a metabolic stress-induced hepatic injury that is closely related to insulin resistance and genetic susceptibility, the pathological changes of which are similar to alcoholic fatty liver disease. NAFLD is a clinicopathological syndrome characterized by steatosis and fat storage of hepatocytes in the hepatic lobule but without history of alcohol abuse. NAFLD shows different degrees of hepatic lesion, from simple fatty liver without any inflammation to severe inflammatory response of severe fibrosis and even cirrhosis, mainly includes 3 types: simple fatty liver, steatohepatitis, fatty cirrhosis.

Non-alcoholic fatty liver disease treatment:
1. Prevention of protopathies or associated risk factors. 2. Basal treatment: developing a reasonable energy intake and diet adjustment, taking moderate aerobic exercises, correcting bad lifestyles and behaviors. 3. Avoiding aggravating hepatic injury: preventing a sharp decline in weight, drug abuse and other factors that may induce exacerbation of hepatopathy. 4. Weight loss: requiring all NAFLD patients who are overweight, and have visceral obesity and rapid weight gain in the short term to change the lifestyles to control weight and reduce waist circumference. Basal treatment for 6 months, weight loss <0.45 kg per month, or body mass index (BMI)>27 $kg/m^2$ combined with blood lipid, blood glucose, blood pressure and other indicators of more than two abnormalities may consider adding sibutramine or orlistat and other obesity drugs, weight loss per week should not exceed 1.2 Kg (children do not exceed 0.5 Kg per week); BMI >40 $kg/m^2$ or BMI >35 $kg/m^2$ combined with sleep apnea syndrome and other obesity-related diseases, may consider the proximal end gastric bypass procedures to lose weight (II-1, II-2, II-3, III). 5. Insulin sensitizer: combined with type 2 diabetes, impaired glucose tolerance, fasting plasma glucose and visceral obesity, may consider the application of metformin and thiazolidinediones in order to improve insulin resistance and control of blood glucose (II-1, II-2, II-3). 6. Hypolipidemic agents: dyslipidemia, with basal treatment and (or) application of weight loss and hypoglycemic drugs for more than 3-6 months, is still mixed with hyperlipidemia or hyperlipidemia, combined with more than 2 risk factors, should consider adding the use of fibrates, statins or probucol and other hypolipidemic drugs (II-1, II-2, II-3). 7. Drugs for hepatopathy: NAFLD associated with hepatic dysfunction, metabolic syndrome, 3-6 months after basal treatment remains ineffective, and liver biopsy shows NASH and chronic progression of the course of the disease, the drug auxiliary treatment for hepatopathy can be used with antioxidant, anti-inflammatory, anti-fibrosis, and related drugs (II-1, II-2, II-3, III) such as polyene phosphatidylcholine, vitamin E, silymarin and ursodeoxycholic acid can be rationally chosen according to drug performance, disease activity and stage of the disease, but multi-drugs should not be applied simultaneously. 8. Liver transplantation: mainly for NASH-related end-stage hepatopathy and some cryptogenic J hepatocirrhosis, and the metabolic condition (III) should be screened before liver transplantation. BMI >40 kg/m$^2$ is contraindication to liver transplantation (III).

The above treatments have not been used by being mixed together, such as a combination of hypoglycemic and hepatopathy drugs, or a combination of lipid-lowering and hepatopathy drugs. Usually, it is not allowed to take the drugs with tea water in the pharmaceutical specification. It is found from our study that the silybin-phospholipid complex preparation can be administrated with a Pu'er tea solution, and the two in combination has synergistic effects for treating non-alcoholic fatty liver diseases.

SUMMARY OF THE INVENTION

The present invention provides a pharmaceutical composition.

The present invention further provides uses of the pharmaceutical composition.

The present invention is achieved by the following technical solutions:

A pharmaceutical composition includes a silybin-phospholipid complex and Pu'er tea.

In the pharmaceutical composition, the silybin-phospholipid complex may be prepared into a pharmaceutical preparation, and the Pu'er tea may be prepared into a tea product; they may also be prepared into a compound pharmaceutical composition together.

Preferably, in the pharmaceutical composition of the present invention, a silybin-phospholipid complex is prepared into a pharmaceutical preparation and a Pu'er tea is prepared into a Pu'er tea product, wherein the pharmaceutical preparation and the Pu'er tea product are placed in a same large package after being separately packaged according to unit dose, and are administrated in combination according to respective doses before use.

In the present invention, when the silybin-phospholipid complex pharmaceutical preparation and the Pu'er tea/Pu'er tea product are administrated in combination, a weight ratio of the administrated silybin-phospholipid complex to the administrated Pu'er tea/Pu'er tea product is (0.5-2.5):(0.3-10), a preferable weight ratio is (1-2):(0.6-5), and a more preferable weight ratio is (1-1.3):1.

In the pharmaceutical composition of the present invention, the silybin-phospholipid complex preparation is a pharmaceutical preparation in a unit dose that can be administrated in combination and is prepared by using the silybin-phospholipid complex as an active pharmaceutical ingredient. Preferably, it is one of drop pill, capsule, soft capsule, granule, and tablet, and most preferably, capsule. Preferably, the silybin-phospholipid complex capsule preparation is prepared according to patent (publication No. CN100594898).

The foregoing weight ratio is the ratio of the weight of the active ingredient of the pharmaceutical preparation, that is, the silybin-phospholipid complex, to the weight of the Pu'er tea/Pu'er tea product.

As a preparation, the silybin-phospholipid complex comprises 10-60% of the total weight of the silybin-phospholipid complex preparation, preferably 30-50%, and more preferably 40%. The silybin-phospholipid complex is formed by silybin and phospholipid in a weight ratio of 1:1-4, and preferably 7:13.

In the pharmaceutical composition of the present invention, the silybin-phospholipid complex, the silybin and phospholipid both belong to prior art, and can be available from the market.

In order to better exert the efficacy of the present invention, the silybin of the present invention is preferably prepared by dissolving silymarin in 80% ethanol, filtering and washing the precipitate with 95% ethanol for three times, collecting the precipitate. The precipitate is dissolved in anhydrous ethanol, filtered, and the filtrate is added with a certain amount of water to separate out the precipitate, and the precipitate is collected by filtration, dried under reduced pressure, pulverized and mixed.

The phospholipid is a phospholipid or lecithin, preferably soybean phospholipid, which is mainly composed of phosphatidylcholine.

In the pharmaceutical composition of the present invention, the Pu'er tea is mainly a Pu'er tea product, such as one of Pu'er tea essence, Pu'er tea leaves, Pu'er tea extract, Pu'er tea cream, Pu'er tea drink, and Pu'er tea bag, and preferably, Pu'er tea essence or Pu'er tea extract. The preparation of the Pu'er tea essence, Pu'er tea leaves, Pu'er tea extract, Pu'er tea cream, Pu'er tea drink, and Pu'er tea bag are all prepared by a routine method of prior art. Said Pu'er tea essence is the nano-scale pure-natural and high-power Pu'er tea essence that is prepared by means of a perfect combination of ecological plantation and biotechnologies, and the Pu'er tea essence is rich in Pu'er factors formed by means of accurate distribution of tea polyphenol, tea pigment, tea polysaccharide, and caffeine. The Pu'er tea essence is available from the market, and preferably a DEEPURE® Pu'er tea essence. It is prepared according to the method of patents (publication No. CN101961061A, CN101961061B, CN101961425A, CN101961425B, CN101961060A, CN101961059A, and CN101961059B).

For example, said Pu'er tea essence is prepared as follows:

Step 1, Pu'er tea leaves are decocted with 6-12 times the volume of water for 2-4 times, 0.5-2 hours each time; extract solution is filtered, and filtrate is concentrated under reduced pressure and the temperature of ≤70° C. to the weight of tea leaves:the volume of concentrate=1:2-1:3;

Step 2, the concentrate is centrifuged with a centrifuge, the centrifugate is concentrated under reduced pressure to density of 1.1-1.25 at 45-65, the concentrated cream is spray dried or microwave dried to obtain the final product.

Preferably, the steps are present as follows:

Step 1, Pu'er tea leaves are decocted with 6-12 times the volume of vigorously boiling water for 3 times, 0.5-2 hours each time; extract solution is filtered, and filtrate is concentrated under reduced pressure and the temperature of ≤70° C. to the weight of tea leaves:the volume of concentrate=1:2-1:3;

Step 2, the concentrate is centrifuged with a tripod pendulum type batch centrifugal, the tripod pendulum is centrifuged with a tubular-bowl centrifuge, and the centrifugate is concentrated under reduced pressure to density of 1.1-1.25 at 45-65° C., concentrated cream is spray dried or microwave dried to obtain the final product;

wherein tubular-bowl centrifuge condition is: centrifuge speed: 15000-19000 rpm/min; spray drying conditions are: inlet temperature: 140-190° C., outlet temperature: 75-95° C.

Most preferably, the steps are present as follows:

Pu'er tea leaves are decocted with vigorously boiling water for 3 times, the first time decocted 1.5 h, 10 times the volume of water added; the second time decocted 1.5 h, 8 times the volume of water added; the third time decocted 1 h, 8 times the volume of water added, extract solution is filtered, and filtrate is concentrated under reduced pressure and the temperature of ≤70° C. to the weight of tea leaves: the volume of concentrate=1:2-1:3, the concentrate is centrifuged with a tripod pendulum type batch centrifugal, the tripod pendulum is centrifuged with a tubular-bowl centrifuge, and the centrifugate is concentrated under reduced pressure to density of 1.1-1.25 at 45-65° C., concentrated cream is spray dried or microwave dried to obtain the final product.

wherein tubular-bowl centrifuge condition is: centrifuge speed: 15000-19000 rpm/min; spray drying conditions are: inlet temperature: 140-190° C., outlet temperature: 75-95° C.

When the pharmaceutical composition of the present invention is used together, the following method may be used, that is, administrating the silybin-phospholipid complex or the silybin-phospholipid complex preparation with a Pu'er tea solution.

The pharmaceutical composition of the present invention is administrated by using the following method: soaking or dissolving any one of the Pu'er tea essence, Pu'er tea leaves, Pu'er tea cream, Pu'er tea drink, and Pu'er tea bag in the composition with a suitable amount of water, and administrating the silybin-phospholipid complex preparation with the Pu'er tea solution by a patient.

The administration method of the present invention overcomes the technical defect of the prior art that tea water and drug cannot be administrated together, or the curative effect of the drug would be reduced. The present invention not only overcomes the technical defect, but also finds that administrating tea water and drug together can generate better curative effects while overcoming the technical defect.

Pu'er tea can improve insulin resistance, regulate the levels of blood lipid and leptin and other effects, can block the fat accumulation of hepatic parenchymal cell caused by insulin resistance to a certain extent, combined with the strong free radical scavenging and anti-oxidative stress ability of silybin, the two have preferable anti-NAFLD (non-alcohol fatty liver) effect.

Hereinafter, beneficial effects of the combination use of the present invention are described by using experimental data.

EXPERIMENTAL EXAMPLES

1 Experimental Animals 60 mice with SPF grade and 6-week-old male C57 BL/6J leptin-deficient (ob/ob), 10 mice with SPF grade and 6 weeks old male C57 BL/6J (ob/m), provided by the Beijing Huafukang Bioscience Co., Inc., raised in Tasly Institute's pharmacological toxicology research center barrier animal room, at the temperature of 20° C.–25° C., relative humidity of 60%, 5 mice in each cage, lighting time of 12 hours, timely and quantitative feed, ob/ob mice are fed with high fat diet (HFD, D12492), C57 BL/6J mice are fed with normal diet, both are provided by Beijing Huafukang Bioscience Co., Inc., and free drinking water, daily replacement of padding.

2 Tested Substances

Silybin-phospholipid complex, provided by Tasly Pharmaceutical Co., Ltd., lot number 500902031; (prepared according to Embodiment 1); Pu'er tea essence, tan powder, provided by Tasly Pharmaceutical Co., Ltd., lot number Z001 PE (2014) C06 (H); stored in the sample cabinet of the test room of Pharmacology Institute to be protected from light at room temperature.

3. Experimental Method 3.1 Experimental Dose Design and Grouping

A human daily dose of a basic product (NAFLMED basic) is 3 g of the silybin-phospholipid complex (including 420 mg of silybin and 780 mg of phospholipid)+1.2 g of Pu'er tea essence. The dose of the silybin-phospholipid complex is 3 g, and upon conversion, the dose of a mouse is 3 g/60*12.3=0.62 g/kg; a human dose of the Pu'er tea essence is 1.2 g; and a high-dose group is additionally set as 2.4 g; upon conversion, the doses of a mouse is 12 g/60*12.3=0.25 g/kg and 2.4 g/60*1230.50 g/kg. Experimental grouping and administration dose design are showed in table 1.

TABLE 1

Experimental grouping and administration doses

| Group | Dose (g/kg) Silybin-phospholipid complex | Dose (g/kg) Pu'er tea essence | Tested animal | The number of animals | Notes |
|---|---|---|---|---|---|
| Normal | — | — | C57 BL/6J | 10 | |
| Model | — | — | ob/ob | 10 | |
| Silybin-phospholipid complex | 0.62 | — | ob/ob | 10 | |
| Low Pu'er tea extract | — | 0.25 | ob/ob | 10 | |
| High Pu'er tea extract | — | 0.50 | ob/ob | 10 | |

TABLE 1-continued

Experimental grouping and administration doses

| Group | Dose (g/kg) | | Tested animal | The number of animals | Notes |
|---|---|---|---|---|---|
| | Silybin-phospholipid complex | Pu'er tea essence | | | |
| Silybin-phospholipid complex + low Pu'er tea extract | 0.62 | 0.25 | ob/ob | 10 | administrated together |
| Silybin-phospholipid complex + high Pu'er tea extract | 0.62 | 0.50 | ob/ob | 10 | administrated together |

3.2 Administration of Tested Substances

After 1 week of adaptive feeding, 60 ob/ob mice of 6-week-old are randomly grouped into 6 groups with 10 in each group. Another 10 6-week-old C57B/6J mice are grouped into a normal group (table 1). Normal group mice are fed with normal diet, and the mice in the model group and the administration group are both fed with high-fat diet (HFD, D12492). In addition, the mice in different drug intervention groups are given the corresponding doses of drugs(table 1) by means of intragastric administration, the normal group and model group are given the same amount of distilled water, the compatibility group of the silybin-phospholipid complex and Pu'er tea extract is administrated together, continuous intragastric administration for 6 weeks.

The mice are free to eat and drink during the experiment, weekly weight, and the doses are adjusted according to the body weight. After the last administration, fasting for 12 h, but water is given, weighing the body weight, extracting rats' eyeballs to collect blood and then put them to death by breaking their necks, and the liver is harvested rapidly, physiological saline rinsing, filter paper blotting and preserved in a −20° C. refrigerator after weighing.

3.3 Detecting Indicators and Methods 3.3.1 General Observation

The weights of mice in each group are measured weekly during the experiment.

3.3.2 Calculation of the Liver Index and Observation of the General Morphology of the Liver After finishing the experiment, the liver is weighed and the liver index is calculated, the liver index (%)=liver wet weight/body weight*100%.

3.3.3 Determination of Serum Biochemical Indexes

Blood of all the mice are collected by extracting rats' eyeballs and centrifuged at 3000 r/min for 15 minutes, the serum is separated and collected in an EP tube and stored at −20° C. refrigerator for later use. The content of glutamic oxaloacetic transaminase (AST), glutamicpyruvic transaminase (ALT), triglyceride (TG), total cholesterol (TC), high-density lipoprotein cholesterol (HDL-C), low-density lipoprotein cholesterol (LDL-C), and glucose (GLU) in serum are measured by 7020 automatic biochemistry instrument.

3.3.4 Insulin Resistant Index

Serum FINS is detected using the Elisa kit and the insulin resistance index is calculated by the formula.

$$Home-IR = \frac{FBG \times FINS}{22.5}$$

3.3.5 Liver Histopathological Examination

Frozen sections are prepared from frozen liver tissue and the degree of hepatic steatosis is observed by oil red O staining. Oil red O staining operation steps: frozen slicing-→sufficiently washing with distilled water→staining with oil red O diluent in the dark for 10-15 minutes→taking out 6 ml of oil red O saturated liquid, adding 4 ml of distilled water, leaving it for 5-10 minutes and filtrating for later use→differentiating to interstitial clear under mirror with 60% ethanol→washing with water→nuclear counter staining with hematoxylin→washing with water→sealing piece with neutral gum→microscope observation.

3.4 Data Processing

SPSS 15.0 statistical software is used for analysis, the data are expressed as mean±standard deviation, the t test is used to analyze whether there's any difference between the two groups before and after treatment or not, and the difference is statistically significant with P<0.05.

4 Experimental Results 4.1 the Effects of Each Tested Substance on Body Weight

The weight of mice in each group are measured weekly during the experiment, and the effects of each tested substance on body weight of non-alcoholic fatty liver mice are investigated. As shown in Table 2, the weight of normal group mice is increased slowly and the weight of model group mice is increased more rapidly. After 6 weeks of administration, except for the silybin-phospholipid complex group, the other groups could inhibit the weight increases of mice in different degrees (P<0.01), and there is no significant difference between each groups.

TABLE 2

Effects of each tested substance on weights of mice (g, n = 10, x̄ ± S)

| Group | Before administration | Administration for 2 weeks | Administration for 4 weeks | Administration for 6 weeks |
|---|---|---|---|---|
| Normal | 21.15 ± 0.79 | 22.59 ± 1.15 | 24.39 ± 1.48 | 26.48 ± 1.73 |
| Model | 44.41 ± 1.76 | 53.18 ± 1.52 | 61.20 ± 1.53 | 65.98 ± 1.69 |
| Silybin-phospholipid complex | 44.42 ± 2.58 | 54.22 ± 1.45 | 61.75 ± 2.01 | 66.84 ± 2.01 |

TABLE 2-continued

Effects of each tested substance on weights of mice (g, n = 10, x̄ ± S)

| Group | Before administration | Administration for 2 weeks | Administration for 4 weeks | Administration for 6 weeks |
|---|---|---|---|---|
| Low silybin-phospholipid complex and Pu'er tea extract | 44.43 ± 2.87 | 51.13 ± 2.36* | 55.62 ± 2.40** | 58.02 ± 2.53** |
| High silybin-phospholipid complex and Pu'er tea extract | 44.40 ± 2.00 | 48.88 ± 2.25** | 55.40 ± 2.26** | 58.05 ± 2.99** |

*compared with the model group, $P < 0.05$;
**compared with the model group, $P < 0.01$;

4.2 the Effects of Each Tested Substance on Liver Index

As shown in Table 3, the body weight, liver wet weight and liver index of mice in the model group are significantly increased (P<0.01) compared with those in the normal group, and each tested substance can significantly reduce the wet weight and liver index of the mice (P<0.01).

glucose of mice in the model group is obviously higher than that of the normal group (p<0.01). After 6 weeks of administration, except for the silybin-phospholipid complex group, other administration groups all can reduce the blood glucose of mice to different degrees (P<0.01). There is no significant difference among the groups.

TABLE 4

Effects of each test substance on blood glucose of mice (mmol/L, n = 10, x̄ ± S)

| Group | Before administration | Administration for 1 week | Administration for 2 weeks | Administration for 3 week | Administration for 4 weeks | Administration for 5 week | Administration for 6 weeks |
|---|---|---|---|---|---|---|---|
| Normal | 7.87 ± 1.15 | 9.31 ± 1.07 | 8.78 ± 1.21 | 7.87 ± 0.71 | 7.96 ± 0.75 | 7.33 ± 0.33 | 8.24 ± 3.56 |
| Model | 23.95 ± 8.47 | 17.75 ± 4.17 | 16.06 ± 4.54 | 14.16 ± 3.75 | 12.68 ± 2.75 | 12.97 ± 2.49 | 17.33 ± 6.13 |
| Silybin-phospholipid complex | 23.14 ± 5.93 | 17.18 ± 3.25 | 17.71 ± 4.25 | 16.43 ± 4.15 | 13.07 ± 3.98 | 12.29 ± 1.36 | 17.64 ± 8.71 |
| Low silybin-phospholipid complex and Pu'er tea extract | 24.05 ± 2.81 | 13.03 ± 3.53* | 11.40 ± 2.85* | 12.95 ± 3.10 | 11.81 ± 5.15 | 11.61 ± 2.81 | 8.29 ± 1.28** |
| High silybin-phospholipid complex and Pu'er tea extract | 20.14 ± 3.42 | 15.36 ± 3.72 | 13.23 ± 6.12 | 19.04 ± 2.36 | 17.65 ± 7.67 | 20.75 ± 8.19 | 11.54 ± 3.19* |

*compared with the model group, $P < 0.05$;
**compared with the model group, $P < 0.01$;

TABLE 3

Effects of each test substance on liver index of mice

| Group | Weight (g) | Liver wet weight (g) | Liver index % |
|---|---|---|---|
| Normal | 26.14 ± 1.65 | 1.18 ± 0.12 | 4.50 ± 0.25 |
| Model | 68.69 ± 2.31 | 4.50 ± 0.45 | 6.54 ± 0.56 |
| Silybin-phospholipid complex | 70.35 ± 2.7 | 3.87 ± 0.23** | 5.51 ± 0.39** |
| Low silybin-phospholipid complex and Pu'er tea extract | 59.00 ± 2.89** | 2.70 ± 0.41** | 4.57 ± 0.56** |
| High silybin-phospholipid complex and Pu'er tea extract | 62.80 ± 3.60** | 2.87 ± 0.45** | 4.55 ± 0.58** |

*compared with the model goup, $P < 0.05$;
**compared with the model group, $P < 0.01$;

4.3 Effects of Each Tested Substance on Blood Glucose

During the period of experiments, effects of the drugs on the blood glucose of mice with non-alcoholic fatty liver diseases in each group are measured each week. As shown in table 4, during the period of administration, the blood 4.4 Effects of Each Tested Substance on Indexes of Blood Lipid and Liver Functions As shown in table 5, compared with the normal group, TC, LDL, ALT, and AST of serum of the model mice with non-alcoholic fatty liver diseases all are obviously increased (P<0.05); the low dose group of the silybin-phospholipid complex and Pu'er tea extract shows no significant improvement in the abnormally increased indexes (P>0.05); the high dose group of the Pu'er tea extract can reduce TC and LDL-C (P<0.05), but shows no significant improvement in ALT and AST (P>0.05); the high and low dose groups of the silybin-phospholipid complex and Pu'er tea extract can both significantly reduce TC, LDL-C, ALT (P<0.05), and the effect is superior to that of using the two alone.

The blood biochemical results indicate that: variation trends of TG and HDL-C of the animal model serum are inconsistent with that of human, and the subsequent experiments mainly focus on examining four biochemical indexes: TC, LDL, ALT, and AST of the serum.

TABLE 5

Effects of each tested substance on indexes of blood lipid and liver functions of mice

| Group | TC | TG | HDL-C | LDL-C | ALT |
|---|---|---|---|---|---|
| Normal | 3.08 ± 0.21 | 0.78 ± 0.32 | 2.03 ± 0.17 | 0.35 ± 0.07 | 30.89 ± 7.66 |
| Model | 11.04 ± 0.96 | 0.50 ± 0.21 | 4.99 ± 0.25 | 2.82 ± 0.45 | 614.03 ± 161.57 |
| Silybin-phospholipid complex | 11.24 ± 0.92 | 0.49 ± 0.19 | 5.07 ± 0.15 | 2.95 ± 0.63 | 695.54 ± 433.13 |
| Low silybin-phospholipid complex and Pu'er tea extract | 9.55 ± 0.79* | 0.18 ± 0.04 | 5.44 ± 0.12 | 2.32 ± 0.511* | 452.80 ± 212.33* |
| High silybin-phospholipid complex and Pu'er tea extract | 7.55 ± 1.16** | 0.28 ± 0.16 | 5.08 ± 0.42 | 1.93 ± 0.43* | 449.71 ± 124.90* |

*compared with the model group, P < 0.05;
**compared with the model group, P < 0.01;

4.5 Effects of Each Tested Substance on Insulin Resistance Indexes

As shown in table 6, insulin resistance indexes of model mice with non-alcoholic fatty liver diseases are obviously increased compared with the normal group (P<0.01); the insulin resistance indexes are not obviously improved while using the silybin-phospholipid complex alone(P>0.05); the Pu'er tea extract and a compatibility group of the Pu'er tea extract and the silybin-phospholipid complex can obviously reduce insulin resistance indexes (P<0.05), and the effect is superior to that of using the silybin-phospholipid complex alone.

TABLE 6

Effects of each tested substance on insulin resistance indexes of mice

| Group | Insulin resistance index |
|---|---|
| Normal | 0.57 ± 0.12 |
| Model | 1.13 ± 0.21 |
| Silybin-phospholipid complex | 0.99 ± 0.37 |
| Low Pu'er tea extract | 0.92 ± 0.26* |
| High Pu'er tea extract | 0.82 ± 0.25** |
| Low silybin-phospholipid complex and Pu'er tea extract | 0.78 ± 0.14** |
| High silybin-phospholipid complex and Pu'er tea extract | 0.68 ± 0.09** |

*compared with the model group, P < 0.05;
**compared with the model group, P < 0.01;

4.6 Effects of Each Tested Substance on Liver Pathology of Mice

Oil red O staining: according to the size and number of red particles in hepatocytes of liver frozen issues stained by Oil red O under light microscope, it is divided into mild, moderate and severe type. Mild, that is, ⅓-⅔ of red granules are shown per unit area under light microscope, graded as 1 point; moderate, that is, more than ⅔ of the hepatocytes containing red particles, graded as 2 points; severe, that is, almost all of the hepatocytes containing red particles, graded as 3 points; no steatosis is observed, graded as 0 points.

As shown in table 7, steatosis occurs in nearly all the hepatocytes in the liver tissues of the model group, and the pathological scores are obviously higher than those of the normal group (P<0.01); the liver pathological scores are not obviously improved while using the silybin-phospholipid complex or the Pu'er tea extract alone(P>0.05); a combined use of the two can obviously improve liver steatosis, reduce the pathological scores (P<0.05), and the effect is superior to using the two alone.

TABLE 7

Effects of each test substance on liver pathology of mice

| Group | Oil red O staining pathological score |
|---|---|
| Normal | 0.000 ± 0.000 |
| Model | 2.800 ± 0.447 |
| Silybin-phospholipid complex | 2.800 ± 0.447 |
| Low Pu'er tea extract | 2.400 ± 0.548 |
| High Pu'er tea extract | 2.600 ± 0.894 |
| Low silybin-phospholipid complex and Pu'er tea extract | 1.800 ± 0.447** |
| High silybin-phospholipid complex and Pu'er tea extract | 1.600 ± 0.894* |

*compared with the model group, P < 0.05;
**compared with the model group, P < 0.01;

5 Experimental Conclusions

The above experimental results show that: the body weight, liver index, blood lipid, ALT, AST and insulin resistance index are significantly increased in the mice of the non-alcoholic fatty liver model group compared with those in the blank group, and the liver tissues are severe steatosis. Pu'er tea can improve insulin resistance, regulate blood lipids, combined with the strong free radical scavenging and anti-oxidative stress ability of silybin, the combination use of the two has improved liver steatosis significantly, and the effect is better than that of the two used alone, and having synergistic effect.

DETAILED DESCRIPTION OF THE INVENTION

Hereinafter, detailed description of the present invention will be described in further detail with reference to embodiments so as to more clearly describe the advantages and features of the present invention. But these embodiments are only exemplary and are not intended to limit the scope of the present invention. It will be understood by those skilled in the art that various modifications and substitutions may be made to the details and forms of the present invention without departing from the spirit and scope of the present invention, but that such modifications and substitutions fall within the scope of the present invention. The present invention is further illustrated by the following specific embodiments, but is not intended to be limiting of the present invention.

Embodiment 1 Preparation of the Silybin-Phospholipid Complex 420 g of silybin and 780 g of granulesten are added into 7,200 ml of anhydrous ethanol; the solution is clarified by heating reflux, concentrated under reduced pressure at 60° C. to a thick shape, obtaining the silybin-phospholipid complex.

Embodiment 2 Preparation of the Silybin-Phospholipid Complex 1,050 g of silybin and 1,050 g of granulesten are added into 10,500 ml of anhydrous ethanol; the solution is clarified by heating reflux, concentrated under reduced pressure at 40° C. to a thick shape, obtaining the silybin-phospholipid complex.

Embodiment 3 Preparation of the Silybin-Phospholipid Complex 3,500 g of silybin and 14,000 g of granulesten are added into 86,100 ml of anhydrous ethanol; the solution is clarified by heating reflux, concentrated under reduced pressure at 80° C. to a thick shape, obtaining the silybin-phospholipid complex.

Embodiment 4 Preparation of the Silybin-Phospholipid Complex 350 g of silybin and 1,400 g of granulesten are added into 20,500 ml of anhydrous ethanol; the solution is clarified by heating reflux, concentrated under reduced pressure at 50° C. to a thick shape, obtaining the silybin-phospholipid complex.

Embodiment 5 Preparation of the Silybin-Phospholipid Complex 350 g of silybin and 650 g of granulesten are added into 10,500 ml of anhydrous ethanol; the solution is clarified by heating reflux, concentrated under reduced pressure at 60° C. to a thick shape, obtaining the silybin-phospholipid complex.

Embodiment 6 Preparation of the Silybin-Phospholipid Complex 350 g of silybin and 650 g of granulesten are added into 6,000 ml of anhydrous ethanol; the solution is clarified by heating reflux, concentrated under reduced pressure at 60° C. to a thick shape, obtaining the silybin-phospholipid complex.

Embodiment 7 Preparation of the Silybin-Phospholipid Complex Capsules

Taking the silybin-phospholipid complex of embodiment 1, adding into 1,200 g of lactose, 450 g of talcum powder, and 150 g of carboxymethyl starch sodium (CMS), and spraying granulation, drying, and smashing are performed at 65° C. to obtain capsule fillers, which are sub-packaged into No. 000 capsules, obtaining 4,000 capsules with 0.75 g for each.

Embodiment 8 Preparation of the Silybin-Phospholipid Complex Capsules

Taking the silybin-phospholipid complex in any one of embodiments 2-6, adding into 70,000 g of lactose, 40,000 g of talcum powder, and 65,000 g of carboxymethyl starch sodium (CMS), and spraying granulation, drying, and smashing are performed at 50° C. to obtain capsule fillers.

Embodiment 9 Preparation of the Silybin-Phospholipid Complex Capsules

Taking the silybin-phospholipid complex in any one of embodiments 1-6, adding into 1,000 g of lactose, 375 g of talcum powder, and 125 g of carboxymethyl starch sodium (CMS), and spraying granulation, drying, and smashing are performed at 75° C. to obtain capsule fillers.

Embodiment 10 Preparation of the Silybin-Phospholipid Complex Tablets

Taking the silybin-phospholipid complex of embodiment 1, adding into 1,050 g of microcrystalline cellulose, 300 g of starch, 200 g of aerosol, 150 g of talcum powder, and 100 g of magnesium stearate, and then the ingredients are mixed uniformly to be pressed into 4,000 tablets.

Embodiment 11 Preparation of the Silybin-Phospholipid Complex Soft Capsules

Taking 100 g of gelatin, 30 g of glycerinum, and 130 g of water, taking the gelatin and adding into a suitable amount of water to make the gelatin expand into liquid gelatin. Taking 600 g of the silybin-phospholipid complex of embodiment 1 and mixing it with 2,400 g of edible vegetable oil, and sufficiently stirring to obtain oil liquid; placing the prepared liquid gelatin in a liquid gelatin storage tank with the temperature being controlled at 60° C., placing the oil solution in a liquid pharmaceutical storage tank, and preferably, the liquid paraffin temperature is 10-17° C. Starting the pill dropping, drying, pill wiping, and packaging to obtain the soft capsules, with the room temperature at 10-20° C. and the dropper temperature at 40-50° C.

Embodiment 12 Preparation of the Silybin-Phospholipid Complex Drop Pills

Taking 500 g of the silybin-phospholipid complex, and 4,500 g of polyethylene glycol 6000, adding into the pharmaceutical fine powder after the matrix melts and mixing uniformly; the temperature is preserved at about 80° C.; dripping the mixture into methylsilicone oil using a drip tube with an inner diameter of 3.3 mm and an outer diameter of 5.1 mm at a dripping speed of 60-70 drops/min; drop pills are collected, and cooling liquids are sucked by filter papers to obtain drop pills.

Embodiment 13 Combined Preparation

Placing 1.5 g of the silybin-phospholipid complex capsules of embodiment 7 and 0.6 g of Pu'er tea essence together in a medicine box, and the unit dose is given.

Embodiment 14 Combined Preparation

Placing 1.5 g of the silybin-phospholipid complex capsules of embodiment 7 and 0.9 g of Pu'er tea essence together in a medicine box, and the unit dose is obtained.

Embodiment 15 Combined Preparation

Placing 0.5 g of the silybin-phospholipid complex capsules of embodiment 7 and 10 g of Pu'er tea together in a medicine box, and the unit dose is given.

Embodiment 16 Combined Preparation

Placing 2.5 g of the silybin-phospholipid complex capsules of embodiment 7 and 5 g of Pu'er tea together in a medicine box, and the unit dose is given.

Embodiment 17 Combined Preparation

Placing 1.5 g of the silybin-phospholipid complex capsules of embodiment 8 and 0.6 g of Pu'er tea essence together in a medicine box, and the unit dose is given.

Embodiment 18 Combined Preparation

Placing 1.5 g of the silybin-phospholipid complex capsules of embodiment 8 and 5 g of Pu'er tea bag are placed together in a medicine box, and the unit dose is obtained.

Embodiment 19 Combined Preparation

Placing 1.5 g of the silybin-phospholipid complex capsules of embodiment 9 and 5 g of Pu'er tea bag together in a medicine box, and the unit dose is obtained.

Embodiment 20 Combined Preparation

Placing 1.5 g of the silybin-phospholipid complex soft capsules of embodiment 11 and 0.6 g of Pu'er tea extract together in a medicine box, and the unit dose is obtained.

Embodiment 21 Combined Preparation

Placing 1.5 g of the silybin-phospholipid complex tablets of embodiment 10 and 0.6 g of Pu'er tea extract together in a medicine box, and the unit dose is obtained.

Embodiment 22 Combined Preparation

Placing 1.5 g of the silybin-phospholipid complex drop pills of embodiment 12 and 0.6 g of Pu'er tea extract together in a medicine box, and the unit dose is obtained.

The invention claimed is:

1. A pharmaceutical composition comprising biologically active ingredients consisting of a silybin-phospholipid complex pharmaceutical preparation and a Pu'er tea essence or aqueous extract,
wherein the silybin-phospholipid complex pharmaceutical preparation and the Pu'er tea essence or aqueous extract are each contained in separate packages according to unit dose,
wherein the separate packages are further contained in a single package,
wherein the ratio of the silybin-phospholipid complex to the Pu'er tea essence or Pu'er tea extract is 0.5-2.5: 0.3-10 (w:w),
wherein the silybin-phospholipid complex pharmaceutical preparation and the Pu'er tea essence or aqueous extract are administrated in a combination according to respective doses to a subject in need thereof.

2. The pharmaceutical composition according to claim 1, wherein the weight ratio of the silybin-phospholipid complex to the Pu'er tea essence or aqueous extract is 1-2:0.6-5.

3. The pharmaceutical composition according to claim 1, wherein the weight ratio of the silybin-phospholipid complex to the Pu'er tea essence or aqueous extract is (1-1.3):1.

4. The pharmaceutical composition according to claim 1, wherein the silybin-phospholipid complex preparation comprises 10-60% of the total weight of the pharmaceutical composition.

5. The pharmaceutical composition according to claim 1, wherein the weight ratio of silybin to phospholipid is 1:1-4 in the silybin-phospholipid complex, or wherein the weight ratio of silybin to phospholipid is 7:13 in the silybin-phospholipid complex.

6. The pharmaceutical composition according to claim 1 wherein the silybin-phospholipid complex pharmaceutical preparation is a drop pill, capsule, soft capsule, granule, or tablet.

7. The pharmaceutical composition according to claim 1, wherein the combination consists of the silybin-phospholipid complex preparation and the Pu'er tea essence or aqueous extract.

8. A method of treating a non-alcoholic fatty liver disease, comprising administering a therapeutically effective amount of the pharmaceutical composition of claim 1 to a human in need thereof.

9. The pharmaceutical composition according to claim 1, wherein the silybin-phospholipid complex pharmaceutical preparation is a drop pill, capsule, soft capsule, granule, or tablet.

10. The pharmaceutical composition according to claim 1, wherein the silybin-phospholipid complex comprises 30-50% of the total weight of the silybin-phospholipid complex pharmaceutical preparation.

11. The pharmaceutical composition according to claim 1, wherein the silybin-phospholipid complex comprises 40% of the total weight of the silybin-phospholipid complex pharmaceutical preparation.

12. The pharmaceutical composition according to claim 4, wherein the weight ratio of silybin to phospholipid is 1:1-4 in the silybin-phospholipid complex, or wherein the weight ratio of silybin to phospholipid is 7:13 in the silybin-phospholipid complex.

13. A method of treating a non-alcoholic fatty liver disease, comprising administering a therapeutically effective amount of the pharmaceutical composition of claim 4 to a human in need thereof.

14. The pharmaceutical composition according to claim 1, wherein the silybin-phospholipid complex comprises 10-60% of the total weight of the silybin-phospholipid complex pharmaceutical preparation.

15. The pharmaceutical composition according to claim 1, wherein the weight ratio of silybin to phospholipid is 1:1-4 in the silybin-phospholipid complex, or wherein the weight ratio of silybin to phospholipid is 7:13 in the silybin-phospholipid complex.

16. A method of treating a non-alcoholic fatty liver disease, comprising administering a therapeutically effective amount of the pharmaceutical composition of claim 2 to a human in need thereof.

17. The pharmaceutical composition according to claim 2, wherein the silybin-phospholipid complex comprises 10-60% of the total weight of the silybin-phospholipid complex pharmaceutical preparation.

* * * * *